(12) United States Patent
Gokingco et al.

(10) Patent No.: US 9,942,848 B2
(45) Date of Patent: Apr. 10, 2018

(54) BI-DIRECTIONAL COMMUNICATIONS IN A WEARABLE MONITOR

(71) Applicant: Silicon Laboratories Inc., Austin, TX (US)

(72) Inventors: Jefferson Lim Gokingco, Austin, TX (US); Moshe Morrie Altmejd, Austin, TX (US)

(73) Assignee: Silicon Laboratories Inc., Austin, TX (US)

( * ) Notice: Subject to any disclaimer, the term of this patent is extended or adjusted under 35 U.S.C. 154(b) by 94 days.

(21) Appl. No.: 14/562,111

(22) Filed: Dec. 5, 2014

(65) Prior Publication Data

US 2016/0165333 A1    Jun. 9, 2016

(51) Int. Cl.
*H04R 3/00* (2006.01)
*H04R 29/00* (2006.01)
(Continued)

(52) U.S. Cl.
CPC ....... *H04W 52/0229* (2013.01); *A61B 5/0002* (2013.01); *A61B 5/024* (2013.01); *A61B 5/02438* (2013.01); *A61B 5/6815* (2013.01); *H04L 69/28* (2013.01); *H04M 1/6058* (2013.01); *H04M 1/72527* (2013.01); *H04M 1/72558* (2013.01); *H04W 4/008* (2013.01)

(58) Field of Classification Search
CPC ... H04R 3/00; H04R 3/02; H04R 3/04; H04R 29/00; H04R 29/001; H04R 29/004; H04R 2201/107; H04R 2225/55; H04R 2420/07; H04R 25/407; H04L 69/28; H04M 1/6058; H04M 1/72558; H04M 1/72527; H04W 52/02; H04W 4/008
See application file for complete search history.

(56) References Cited

U.S. PATENT DOCUMENTS 5,590,407 A  * 12/1996  Ishikawa ............... H04M 1/725
                                                        340/286.09
8,157,730 B2    4/2012  LeBoeuf et al.
(Continued)

OTHER PUBLICATIONS

Si1141/42/43, "Proximity/Ambient Light Sensor IC with I2C Interface," Silicon Laboratories, Oct. 2014, pp. 1-75.
(Continued)

*Primary Examiner* — Thang Tran
(74) *Attorney, Agent, or Firm* — Zagorin Cave LLP

(57) ABSTRACT

A technique for arbitrating conflicting usage of a communications channel of a wearable communications device is disclosed. In at least one embodiment of the invention, a method includes transmitting a voice signal from a microphone to a portable device using a first communications channel in a first mode of operating a system. The method includes transmitting a monitor signal to the portable device using the first communications channel for a predetermined period of time in response to detection of a beacon signal initiated by an application executing on the portable device. The first and second signals may be ultrasonic signals received over the first communications channel and may have the same frequency and different phases. The beacon signal may be detected based on the first and second signals. The first communications channel may include an audio jack of the portable device.

19 Claims, 6 Drawing Sheets

(51) Int. Cl.
*H04W 52/02* (2009.01)
*A61B 5/00* (2006.01)
*A61B 5/024* (2006.01)
*H04L 29/06* (2006.01)
*H04M 1/60* (2006.01)
*H04M 1/725* (2006.01)
*H04W 4/00* (2018.01)

(56) References Cited

U.S. PATENT DOCUMENTS

| | | | |
|---|---|---|---|
| 8,204,786 | B2 | 6/2012 | LeBoeuf et al. |
| D666,169 | S | 8/2012 | Tucker et al. |
| 8,251,903 | B2 | 8/2012 | LeBoeuf et al. |
| 8,423,112 | B2 | 4/2013 | McKenna et al. |
| 8,512,242 | B2 | 8/2013 | LeBoeuf et al. |
| 8,647,270 | B2 | 2/2014 | LeBoeuf et al. |
| 8,652,040 | B2 | 2/2014 | LeBoeuf et al. |
| 8,700,111 | B2 | 4/2014 | LeBoeuf et al. |
| 8,702,607 | B2 | 4/2014 | LeBoeuf et al. |
| 8,788,002 | B2 | 7/2014 | LeBoeuf et al. |
| 2008/0076972 | A1* | 3/2008 | Dorogusker ....... A61B 5/02055 600/300 |
| 2008/0171945 | A1* | 7/2008 | Dotter ................. A61B 5/024 600/514 |
| 2009/0287067 | A1* | 11/2009 | Dorogusker ....... A61B 5/02055 600/300 |
| 2009/0316529 | A1* | 12/2009 | Huuskonen ............... G01S 5/26 367/124 |
| 2011/0153315 | A1* | 6/2011 | Majumdar ............ G10L 19/002 704/203 |
| 2012/0171963 | A1* | 7/2012 | Tsfaty .................... H04B 11/00 455/41.3 |
| 2012/0278070 | A1* | 11/2012 | Herve ................ G10L 21/0208 704/226 |
| 2012/0308034 | A1* | 12/2012 | El-Hoiydi ............ H04B 7/0671 381/77 |
| 2012/0310394 | A1* | 12/2012 | El-Hoiydi ............ H04B 7/0667 700/94 |
| 2014/0169768 | A1* | 6/2014 | Webb ....................... H04N 5/04 386/285 |
| 2014/0170979 | A1* | 6/2014 | Samanta Singhar ... G10L 25/60 455/41.2 |
| 2014/0233527 | A1* | 8/2014 | Gehring ............... H04R 25/554 370/330 |
| 2015/0063604 | A1* | 3/2015 | Ohbuchi .................. H04R 1/08 381/122 |

OTHER PUBLICATIONS

TS3310, "A True 150-nA 1Q, 0.9-3.6VIN, Selectable 1.8-5VOUT Instant-OnTM Boost Converter," Silicon Laboratories, 2014, pp. 1-18.
Inside Activity Tracking, "Biometrics and Wearables: Enabling the Next Billion Dollar Disruptions," CVC, Sep. 12, 2013 in Commercial, Military & Safety, Internet of Things, Opinion, Research, downloaded on Sep. 17, 2014 from http://www.insideactivitytracking.com/wearables-enable-biometrics-that-will-disrupt-billion-dollar-security-market/, 6 pages.

* cited by examiner

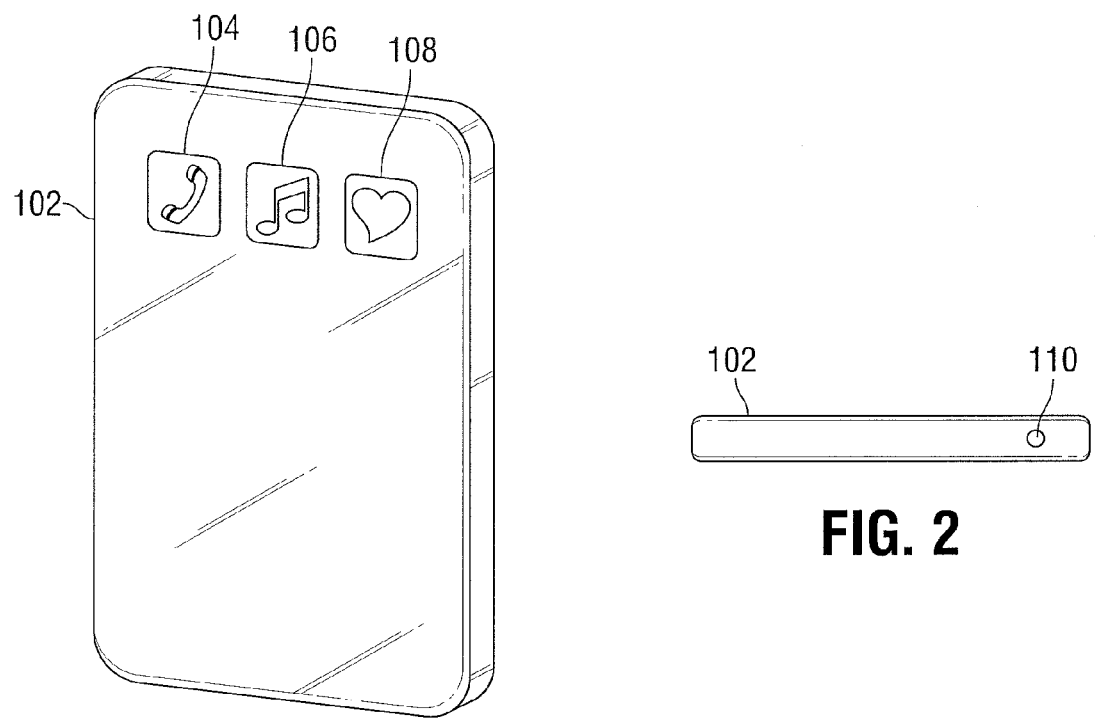
FIG. 2
FIG. 1
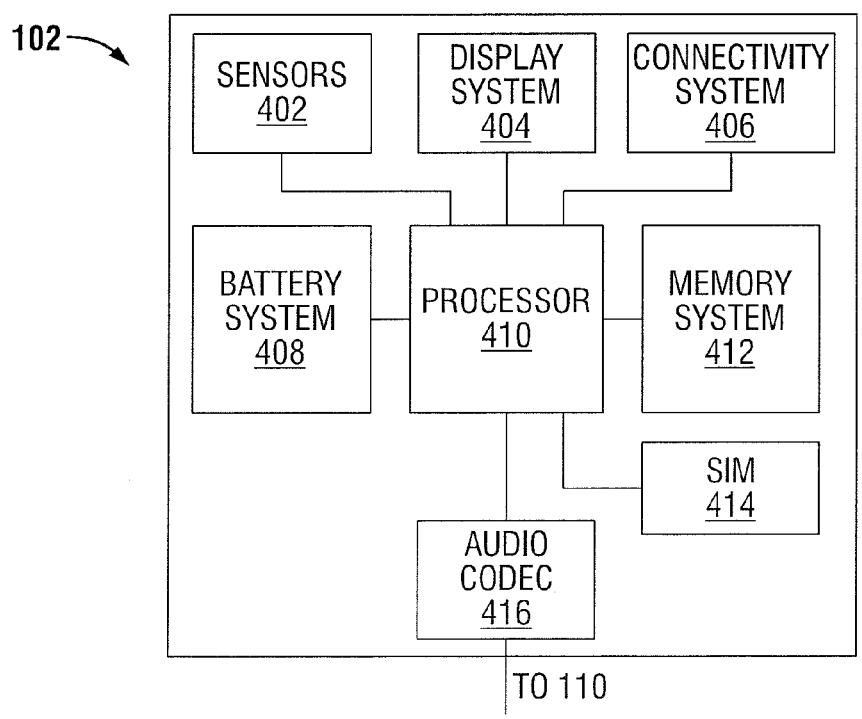
FIG. 3

US 9,942,848 B2

BI-DIRECTIONAL COMMUNICATIONS IN A WEARABLE MONITOR

BACKGROUND

Field of the Invention

This application relates to wearable electronic devices and more particularly to monitor applications in wearable electronic devices.

Description of the Related Art

A wearable electronic device or portable device may include a content delivery system (e.g., an audio player), mobile communications device (smart phone), or clothing and accessories including computer and advanced electronic technologies. A typical wearable electronic device includes a limited number of input/output ports. Adding additional ports to a wearable device may increase size and cost of the wearable device. Accordingly, increasing the functionality of existing input/ports is desired.

SUMMARY OF EMBODIMENTS OF THE INVENTION

A technique for arbitrating conflicting usage of a communications channel of a wearable communications device is disclosed. In at least one embodiment of the invention, a method includes transmitting a voice signal from a microphone to a portable device using a first communications channel in a first mode of operating a system. The method includes transmitting a monitor signal to the portable device using the first communications channel for a predetermined period of time in response to detection of a beacon signal initiated by an application executing on the portable device. The method may include waking a processor of the system from a low-power mode of operation in response to detecting a differential amplitude greater than a predetermined threshold level of a first signal received using a first speaker channel of the first communications channel and a second signal received using a second speaker channel of the first communications channel. The method may include detecting the beacon signal based on the first and second signal. The first and second signals may be ultrasonic signals received over the first communications channel and may have the same frequency and different phases. The beacon signal may be detected based on the first and second signals. The first communications channel may include a microphone jack socket of the portable device.

In at least one embodiment of the invention, an apparatus includes a controller configured to enter a first operational mode from a second operational mode in response to detecting presence of a first ultrasonic tone and a second ultrasonic tone in a signal received from a portable device. The apparatus includes a circuit configured to transmit a first signal received from a microphone to the portable device in the first mode. The circuit is configured to transmit a second signal received from a detector in a first speaker module to the portable device in the second mode. The second operating mode may be a monitoring mode. The portable device may include a processor configured to execute a first application and a second application. The first application may be configured to cause the portable device to transmit the first ultrasonic tone having a first ultrasonic frequency and having a first phase on a first speaker channel and to cause the portable device to transmit the second ultrasonic tone having the first frequency and a second phase on a second speaker channel. The portable device may include an audio jack and the portable device may be configured to combine the first ultrasonic tone with an audio signal provided by a third application executing on the portable device to generate the signal. The signal may be transmitted using the microphone jack socket.

BRIEF DESCRIPTION OF THE DRAWINGS

The present invention may be better understood, and its numerous objects, features, and advantages made apparent to those skilled in the art by referencing the accompanying drawings.

FIG. 1 illustrates an exemplary portable device executing a plurality of exemplary applications.

FIG. 2 illustrates side view of the exemplary portable device of FIG. 1.

FIG. 3 illustrates a functional block diagram of the exemplary portable device of FIG. 1.

The use of the same reference symbols in different drawings indicates similar or identical items.

DETAILED DESCRIPTION

Figure 4:
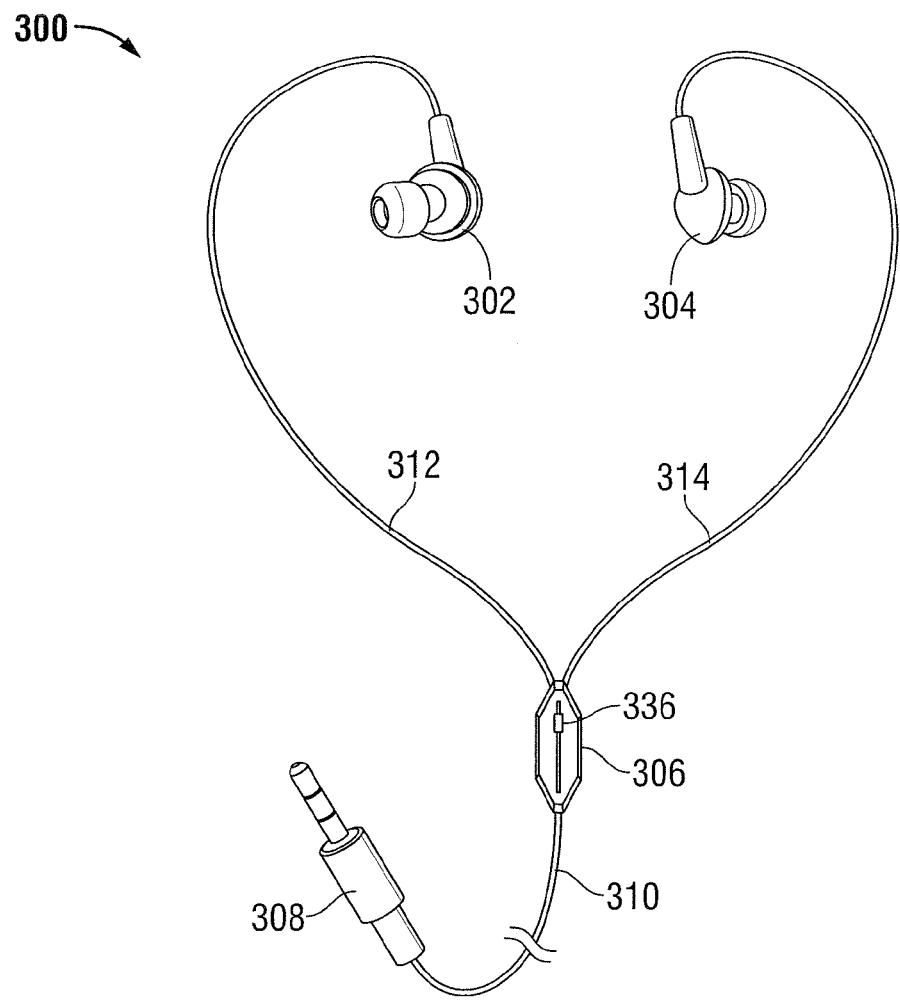
FIG. 4 illustrates an exemplary headset for use with the exemplary portable device of FIG. 1.

Referring to FIGS. 1 and 2, an exemplary portable device is a wearable smart phone communications device (e.g., portable device 102) that executes multiple applications. For example, portable device 102 executes a wireless communications application (e.g., telephony application 104), a content delivery application (e.g., digital audio player application 106), and a monitor application (e.g., heart rate monitor application 108). A typical portable device includes microphone jack socket 110 (e.g., socket, connector, or jack socket) to which a headset may be coupled. The headset typically includes headphones (e.g., earspeakers, earphones, cans, earbuds, or earphones) and a microphone. Referring to FIG. 3, a typical portable device 102 includes processor 410 configured to execute instructions stored in memory system 412. Portable device 102 may include subscriber identity module 414 and connectivity system 406 to facilitate wireless or wired communications consistent with one or more protocols for wide area networks (e.g., a satellite or terrestrial wide area network using e.g., Long-Term Evolution (LTE), second-Generation (2G), third-Generation (3G), fourth-generation (4G), LTE-Advanced, LTE in unlicensed spectrum (LTE-U), Global System for Mobile Communications (GSM), Enhanced Data rates for GSM Evolution (EDGE), High Speed Packet Access (HSPA), Universal Mobile Telecommunications System (UMTS), and Worldwide Interoperability for Microwave Access (WiMax) wireless communications, or other wireless communications protocols, which use one or more of Code Division Multiple access (CDMA), Time Division Multiple Access (TDMA), Frequency Division Multiple Access (FDMA), Wideband CDMA (WCDMA), Orthogonal Frequency Division Multiple Access (OFDMA), or other suitable communications techniques), local area networks (e.g., Institute of Electrical and Electronics Engineers (IEEE) 802.11 standard-compliant networks), or other network protocols. Sensors 402 and display system 404 may be configured to communicate with a user, although other input and output devices (e.g., keyboard) may be included. Audio codec 416 provides output audio signals to microphone jack socket 110.

Figure 5:
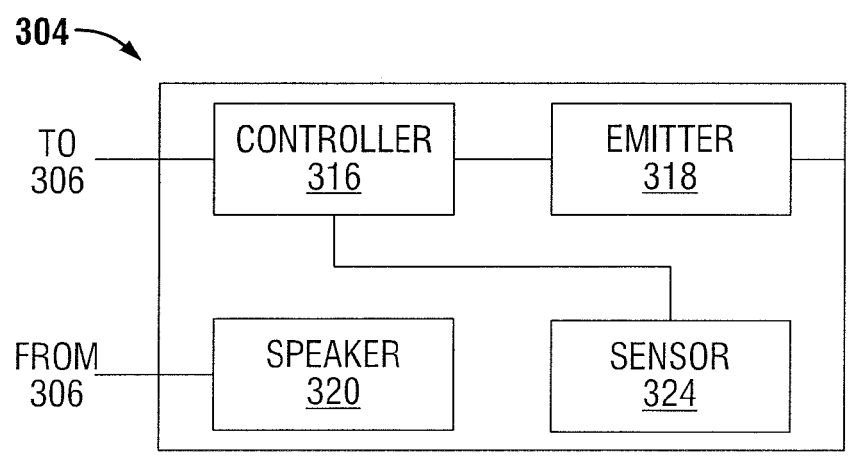
FIG. 5 illustrates a functional block diagram of an exemplary earbud of the exemplary headset of FIG. 4.

Referring to FIGS. 4 and 5, exemplary headset 300 includes in-ear headphones (e.g., earbuds 302 and 304) and microphone module 306, which may be coupled to a portable device via transmission line 310 and microphone jack 308 (e.g., audio jack, phone jack, phone plug, stereo plug, headphone jack, microphone jack, bantam plug, tiny telephone connector, mini-stereo, mini jack, or jack plug). An individual headphone (e.g., earbud 304) includes speaker 320, emitter 318, and controller 316. Headset 300 draws power from a microphone bias circuit of the portable device via a microphone jack socket of the portable device.

Speaker 320 delivers audio signals according to corresponding signals received from a portable device via microphone module 306 and microphone jack 308. For example, referring back to FIG. 1, the audio signals may be based on signals generated by digital audio player application 106 or based on signals generated by telephony application 104. Referring back to FIGS. 4 and 5, in at least one embodiment, headset 300 is configured to operate in a monitor mode and a talk mode. In talk mode, the speakers in earbuds 302 and 304 deliver voice from a remote user and microphone module 306 is configured to transmit local user voice to the portable device. In monitor mode, the speakers in earbuds 302 and 304 may be used to deliver audio to a user from media being provided by the portable device for consumption and microphone module 306 transmits sensor information to the portable device for further processing by the portable device.

In at least one embodiment, earbud 304 includes emitter 318 and sensor 324 for monitoring a physiological parameter (e.g., heart rate). In at least one embodiment, sensor 324 is an optical detector and emitter 318 of earbud 304 is an optical emitter (e.g., light-emitting diode (LED), laser diode, vertical cavity surface emitting laser (VCSEL), semiconductor laser diode or other optical emitter that is configured to emit a beam of light that may be reflected by a medium proximate to or in contact with earbud 304. Sensor 324 generates a signal in response to detection of optical signals, which may include at least some reflected light of an emitted beam of light. That reflected light is reflected by the medium (e.g., tissue of the outer ear when the earbud is inserted into a human ear). Controller 316 digitizes the optical sensor data and transmits an indication of the sensed signal over transmission line 314 to microphone module 306. For example, referring to FIGS. 1, 4, and 5, controller 316 encodes the optical sensor information and sends the information through a Manchester-encoded audio signal to portable device 102 via microphone module 306. Monitor application 108 executing on the portable device receives the Manchester-encoded samples and converts the optical sensor data to a pulse rate, which may be displayed on a screen of the portable device 102 or otherwise communicated to the user.

Figure 6:
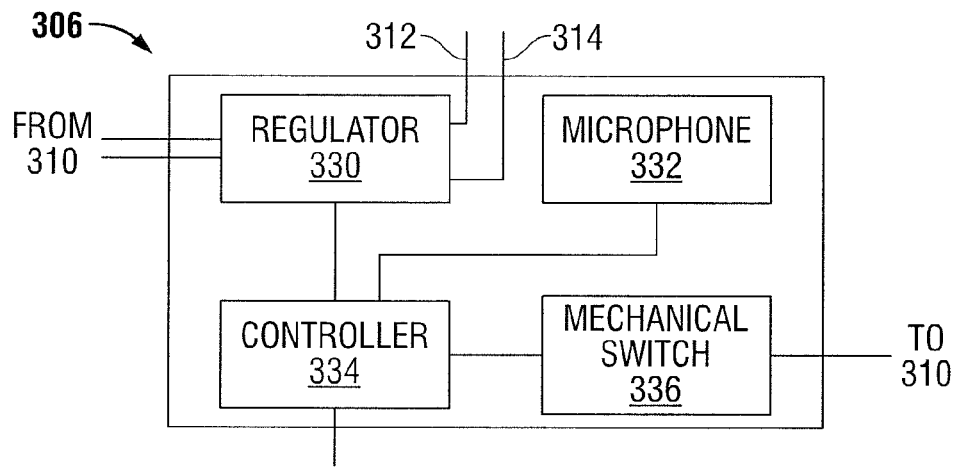
FIG. 6 illustrates a functional block diagram of an exemplary microphone system of the exemplary headset of FIG. 4.

Referring to FIG. 6, microphone module 306 includes regulator 330, which generates appropriate bias signals for microphone module 306 based on that power and a separate power supply may be excluded from headset 300. Microphone module 306 includes microphone 332, which senses audio signals and transmits signals based on the audio signals over a communications channel (e.g., a communications channel using transmission line 310) to portable device 102 over that same communications channel. Note that when the heart rate monitor application is enabled, signals indicative of reflected optical signals are also to be transmitted to portable device 102 over transmission line 310. Microphone module 306 may arbitrate collisions of the signals provided by earbud 304 and the signals provided by microphone 332 based on an input received mechanically from a user via mechanical switch 336. However, such arbitration techniques require a user to remember to flip the switch to configure the device for a telephone conversation. In addition, the user will need to flip the mechanical switch again when the microphone signal (e.g., for telephony operations) is no longer needed to configure the device for heart rate monitoring.

Rather than relying on techniques that require user intervention, an arbitration technique includes automatic control of the microphone interface by a portable device or application executing on the portable device. A typical stereo/microphone interface of a portable device uses left and right speaker channels to deliver audio content to speakers. Therefore, that interface is typically unavailable for communications from the portable device to the microphone module. However, the arbitration technique includes transmission of an inaudible beacon signal (e.g., a signal having frequencies of at least 20 kilo-Hertz) from the portable device to the microphone module to indicate that the monitor mode is enabled.

Figure 7:
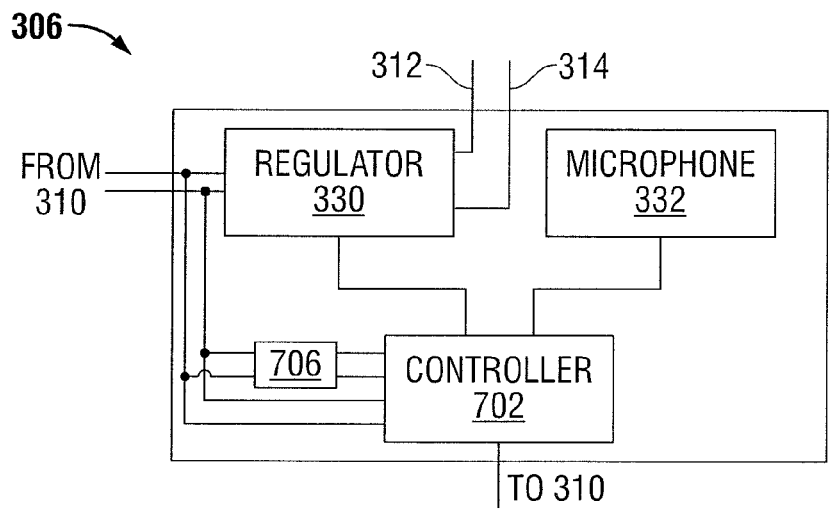
FIG. 7 illustrates a functional block diagram of an exemplary microphone system consistent with at least one embodiment of the invention.
Figure 8:
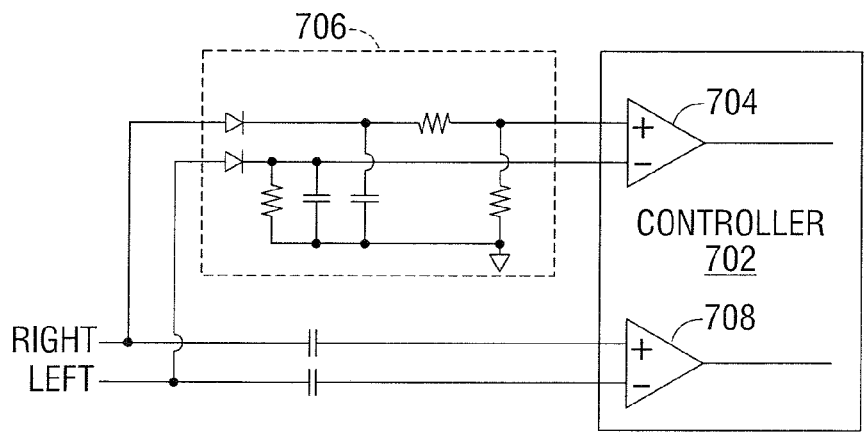
FIG. 8 illustrates a circuit diagram of a portion of an exemplary microphone system consistent with at least one embodiment of the invention.

Referring to FIGS. 7 and 8, microphone module 306 may exclude a mechanical switch and instead includes envelope detector 706, which wakes controller 702 from a low-power state in response to detecting a large differential energy between left and right speaker channels. In response to being powered-up, controller 702 then verifies that the large differential energy is a predetermined beacon signal that indicates that the monitor mode is enabled. For example, controller 702 may include analog-to-digital signal converter that digitizes the received signal. Controller 702 may be configured to process the digital signal to verify that it includes a beacon having a predetermined beacon frequency and cadence.

Still referring to FIGS. 7 and 8, in at least one embodiment, during monitor mode, microphone module 306 detects the beacon signal using both the left and right channel signals. The monitoring application generates inaudible tones, which are combined with audio signals provided by a content delivery application. Since the tones are above the audible frequency range, the tones do not interfere with media consumption by a user. In at least one embodiment, the arbitration technique multiplexes the tones with a corresponding left or right channel signal. A first ultrasonic tone being transmitted with the left channel audio signal is out of phase (e.g., 180 degrees out of phase) with a second ultrasonic tone being transmitted with the right channel audio signal. Controller 702 includes a low power analog comparator 704 that monitors the existence of the ultrasonic tones while still operating at a very low power state. Once controller 702 wakes from the low-power state, controller 702 determines the tone frequencies using an analog-to-digital converter. When controller 702 detects the ultrasonic tones having the predetermined frequency, controller 702 configures the microphone module in a monitor mode.

Figure 9:
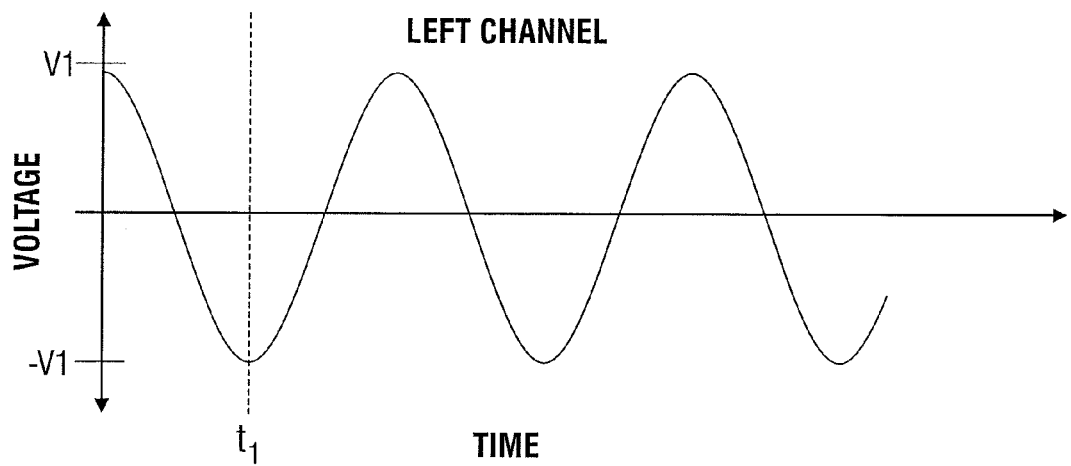
FIGS. 9 and 10 illustrate exemplary waveforms of signals generated by the portable device of FIG. 1 consistent with at least one embodiment of the invention.
Figure 10:
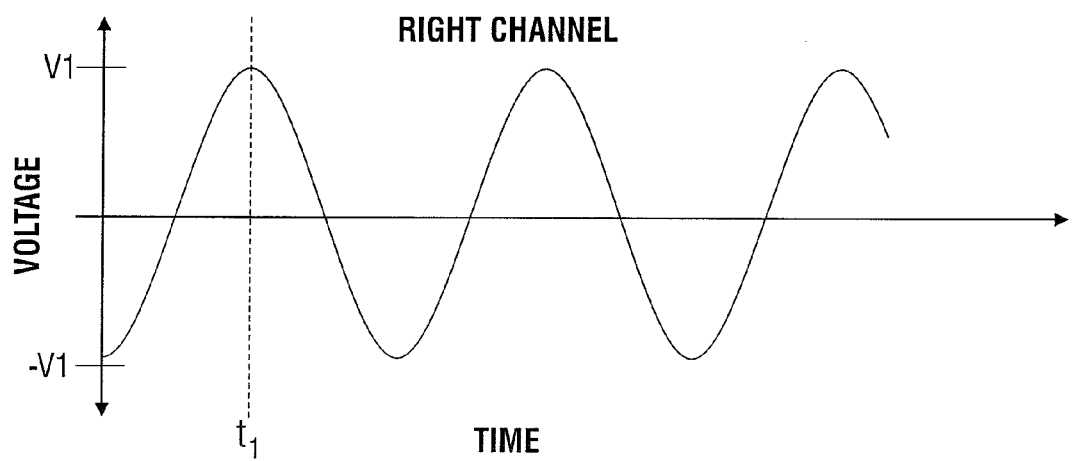

Referring to FIGS. 9 and 10, an exemplary beacon includes a left channel sinusoid and a right channel sinusoid having a particular ultrasonic frequency. The left channel tone is out of phase with the right channel tone. Although the left channel tone and right channel tone are illustrated as being 180 degrees out of phase, other phase differences that result in the envelope detector detecting an energy difference above a predetermined threshold (e.g., a voltage level indicative of a beacon signal and sufficient to wake controller 702) may be used. The tones may be generated by a monitor application executing on processor 410 of portable device 102 of FIG. 3. The monitor application may access predetermined samples of audio data stored in memory system 412, calculate samples of audio data corresponding to those tones from a formula that corresponds to the predetermined tones, or generate those tones using other suitable tone generation technique. The samples may be combined with audio signals, when appropriate, and provided to audio codec 416 for transmission using microphone jack socket 110.

Referring back to FIGS. 7 and 8, in at least one embodiment, in response to detecting the beacon, microphone module 306 transitions from the talk mode to the monitor mode for a predetermined period of time. In response to expiration of the predetermined period of time, microphone module transitions back to talk mode. In at least one embodiment, microphone module 306 detects the beacon using envelope detector 706 and comparators 704 and 708 by determining a difference between signals received on the left and right channels. When the difference exceeds a predetermined threshold level, controller 702 further processes the signals to verify that the beacon signal has been received.

Figure 11:
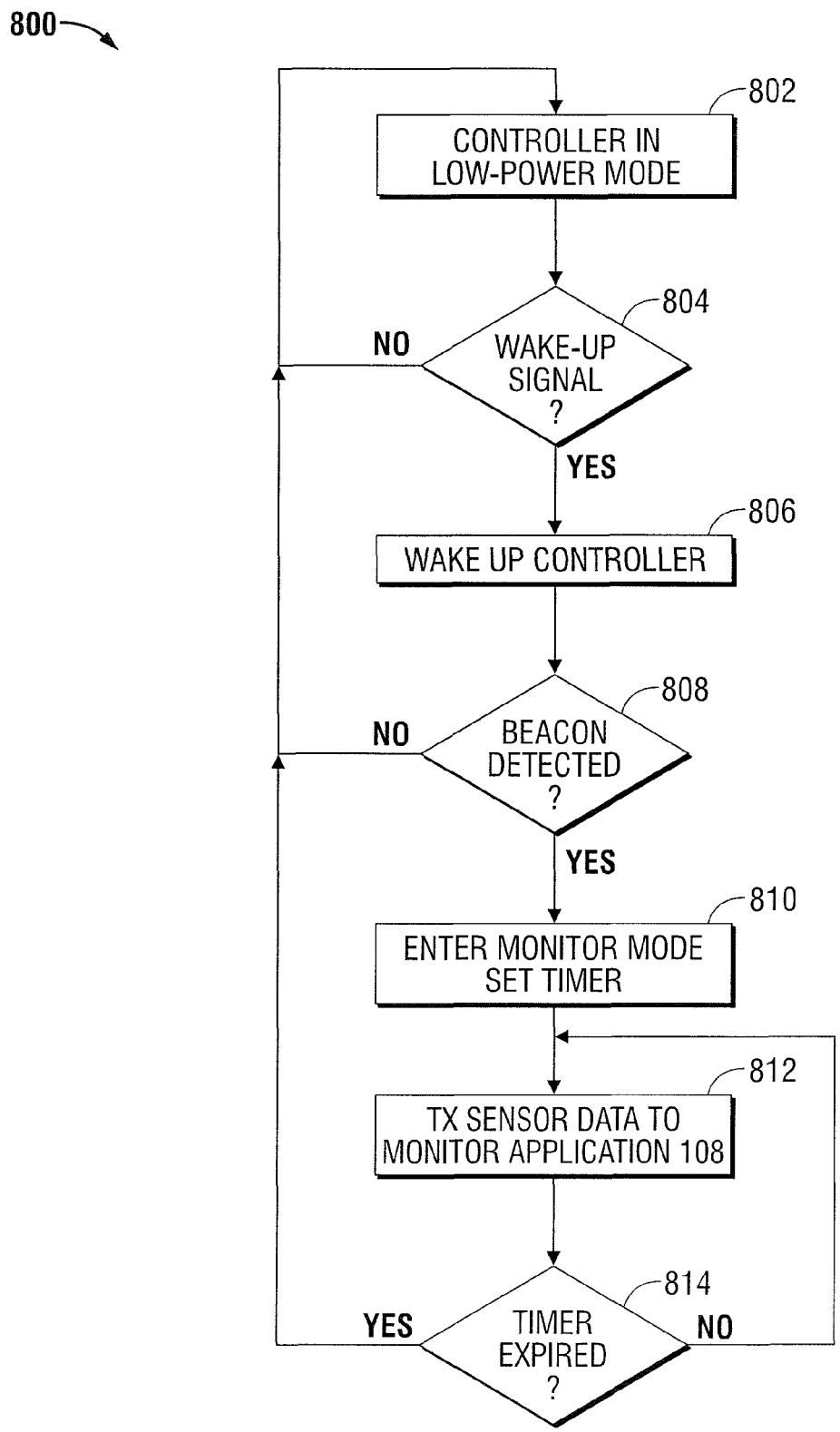
FIG. 11 illustrates information and control flows for the controller of FIG. 7 consistent with at least one embodiment of the invention.

Referring to FIGS. 1, 7, and 11, an exemplary control flow for controller 334 of microphone module 306 maintains controller 702 of microphone module 306 in a low power state (802) until microphone module 306 receives an inaudible wake-up signal (804). A wake-up signal causes controller 702 to transition from the low-power mode to an operating mode in which controller 702 detects whether or not a beacon signal has been received (808). If the beacon is not detected, controller 702 transitions back to the low-power mode (802). If the beacon is detected, controller 702 enters a monitor mode and sets a timer corresponding to the duration of the monitor interval (810). During monitor mode, microphone module 306 transmits sensor data received from earbud 304 to monitor application 108 executing on portable device 102 (812). If the timer expires (814), controller 702 returns to a low-power mode (802). If the timer has not expired (814), controller 702 continues to transmit sensor data to monitor application 108 (812).

Figure 12:
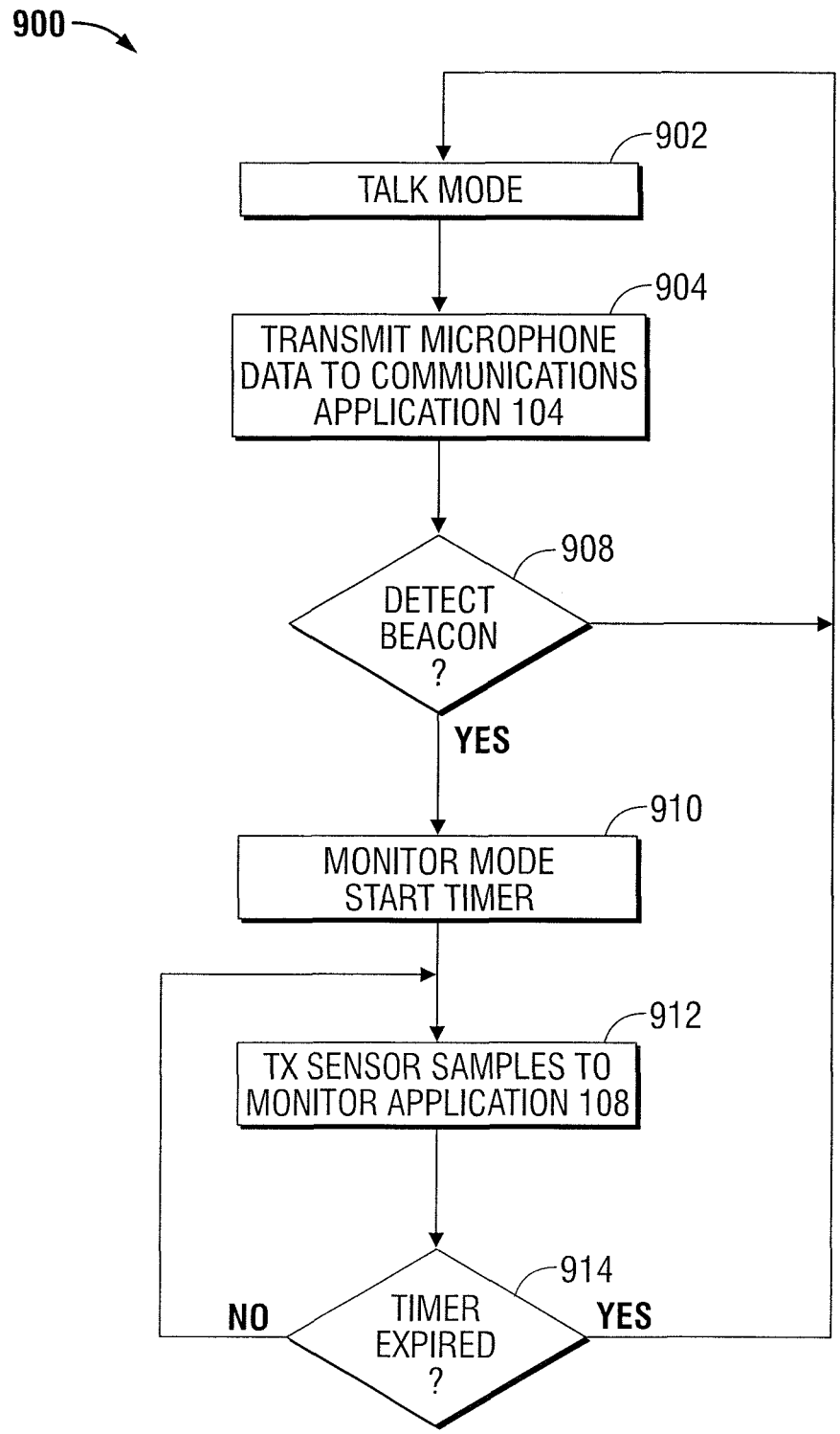
FIG. 12 illustrates information and control flows for the microphone system of FIG. 7 consistent with at least one embodiment of the invention.

Referring to FIGS. 1, 7, and 12, an exemplary control flow for microphone module 306 has a default configuration of being in the talk mode (902). Microphone module 306 transmits microphone data to a communications application executing on the portable device 102 (904). Microphone module 306 remains in the talk mode until the beacon has been detected. In response to controller 702 detecting the beacon (908), microphone module 306 enters the monitor mode and controller 702 starts a timer (910). Microphone module 306 transmits sensor samples to monitor application 108 executing on portable device 102. Microphone module 306 remains in the monitor mode until the timer expires (914). In response to expiration of the timer (914) microphone module returns to the talk mode (902).

Note that in other embodiments, microphone module 306 may use other techniques to initiate a mode change between monitor mode and talk mode. For example, the beacon may only be transmitted by the monitor application for a predetermined duration and detection of the beacon may be used to toggle the mode from monitor mode to talk mode or from talk mode to monitor mode rather than only to enable the monitor mode. Maintaining controller 702 in a low-power mode when microphone module 306 is in talk mode reduces power consumption of the arbitration technique and conserves battery life as compared to other embodiments (e.g., embodiment of FIG. 6) in which controller 702 is fully operational in both monitor mode and talk mode.

Thus, a power-efficient technique for communication of a monitor that coexists with audio media consumption with reduced user interaction has been disclosed. Structures described herein may be implemented using software executing on a processor (which includes firmware) or by a combination of software and hardware. Software, as described herein, may be encoded in at least one non-transitory computer readable medium. As referred to herein, a non-transitory computer-readable medium includes at least a disk, tape, or other magnetic, optical, or electronic storage medium.

The description of the invention set forth herein is illustrative, and is not intended to limit the scope of the invention as set forth in the following claims. For example, while the invention has been described in an embodiment in which an optical emitter and sensor are used, one of skill in the art will appreciate that the teachings herein can be utilized with emitters and sensors corresponding to other electromagnetic signals. In addition, while the invention has been described in an embodiment in which a heart rate monitor application is realized, one of skill in the art will appreciate that a wearable device may include additional emitters and sensors for signals of the same or different wavelengths configured to provide indicators of other physiological or environmental parameters (e.g., pulse, blood-oxygen level, etc.) and the portable device may include a monitor application to process those indicators accordingly. Moreover, although the invention has been described in an embodiment in which a portable device is used, one of skill in the art will appreciate that the teachings herein can be utilized with stationary devices that receive conflicting signals on the same port. Variations and modifications of the embodiments disclosed herein, may be made based on the description set forth herein, without departing from the scope and spirit of the invention as set forth in the following claims.

What is claimed is:

1. A method for arbitrating signals in a headset, the method comprising:
receiving a voice signal from a microphone;
transmitting the voice signal using a communications channel in a talk mode of operating the headset;
detecting a beacon signal;
operating the headset in a monitor mode in response to the detected beacon signal;
receiving a sensor signal including sensed data indicative of a physiological parameter in the monitor mode of operating the headset; and
transmitting a monitor signal using the communications channel for a predetermined period of time in the monitor mode of operating the headset, the monitor signal including the sensed data.

2. The method, as recited in claim 1, further comprising:
receiving a first signal using a first speaker channel of the communications channel;
receiving a second signal using a second speaker channel of the communications channel;
detecting a differential amplitude of the first signal and the second signal greater than a predetermined threshold; and
waking a processor from a low-power mode of operation in response to the detected differential amplitude,
wherein the beacon signal is detected based on the first signal and the second signal.

3. The method, as recited in claim 2, wherein the first and second signals are ultrasonic signals received over the communications channel and have the same frequency and different phases.

4. The method, as recited in claim 1, wherein the communications channel is coupled to a microphone jack socket of a portable device.

5. The method, as recited in claim 1, further comprising:
sensing the data indicative of the physiological parameter using a sensor in an earpiece of the headset; and
wherein the sensor signal is received from the earpiece, the monitor signal being based on the sensed data.

6. The method, as recited in claim 5, further comprising:
receiving a first signal using a first speaker channel,
wherein the first signal comprises an audio signal and an ultrasonic signal.

7. The method, as recited in claim 1, further comprising:
providing physiological information to a display on a portable device coupled to the headset, the physiological information being based on the sensed data; and
providing voice information based on the voice signal to an audio application executing on the portable device.

8. The method, as recited in claim 1, further comprising:
executing an application on a portable device coupled to the headset, the application being a physiological parameter monitoring application responsive to the monitor signal; and
executing a voice communications application on the portable device responsive to the voice signal.

9. An apparatus comprising:
a microphone configured to transmit a voice signal; and
means for arbitrating signals in a headset, the means for arbitrating being configured to receive audio signals, the voice signal, ultrasonic signals, and a sensed signal, the means for arbitrating signals being further configured to detect a beacon signal based on the ultrasonic signals and to transmit a monitor signal for a predetermined period of time in response to the detected beacon signal,
wherein the monitor signal is based on sensed data included in the sensed signal, the sensed data being indicative of a physiological parameter.

10. The apparatus, as recited in claim 9, further comprising:
a portable device configured to execute an application configured to generate the ultrasonic signals and configured to receive the monitor signal.

11. An apparatus comprising: a microphone configured to transmit a voice signal; a communications channel; and a circuit configured to receive the voice signal from the microphone and configured to transmit the voice signal using the communications channel, the circuit being further configured to generate a monitor signal, to detect a beacon signal, and to transmit the monitor signal using the communications channel for a predetermined period of time in response to detection of the beacon signal by the circuit, the circuit being further configured to receive a first signal using a first speaker channel, receive a second signal using a second speaker channel, and receive a sensed signal using the first speaker channel, the monitor signal being based on the sensed signal, and the beacon signal being based on the first signal and the second signal.

12. The apparatus, as recited in claim 11, wherein the circuit comprises:
a controller; and
an envelope detector,
wherein the circuit is configured to wake the controller from a low-power mode of operation in response to detecting a differential amplitude of a first signal and a second signal greater than a predetermined threshold level the first signal being received using a first speaker channel of the communications channel and the second signal being received using a second speaker channel of the communications channel, and
wherein the circuit is further configured to use the envelope detector and the controller to detect the beacon signal based on the first signal and the second signal.

13. The apparatus, as recited in claim 12, wherein the first and second signals are ultrasonic signals received over the communications channel and have the same frequency and different phases and the beacon signal is detected based on the first and second signals.

14. The apparatus, as recited in claim 11, wherein the communications channel is coupled to a microphone jack socket of a portable device.

15. The apparatus, as recited in claim 11, wherein the first signal comprises an audio signal and an ultrasonic signal.

16. The apparatus, as recited in claim 11, further comprising: a portable device configured to provide physiological information to a display on the portable device, the physiological information being based on the monitor signal, the portable device being configured to provide voice information based on the voice signal to an audio application executing on the portable device.

17. The apparatus, as recited in claim 11, further comprising:
a portable device coupled to the circuit via the communications channel, the portable device comprising a processor configured to execute a physiological parameter monitoring application responsive to the monitor signal and the processor being configured to execute a voice communications application responsive to the voice signal.

18. The apparatus, as recited in claim 11, further comprising:
a first speaker module comprising:
a first speaker configured to provide a first audio signal; and
an optical emitter configured to emit signals in a first frequency range;
an optical detector configured to detect signals in the first frequency range; and
a processor configured to communicate a signal to the circuit based on the signals detected by the optical detector.

19. The apparatus, as recited in claim 11, further comprising:
a portable device,
wherein the portable device comprises a microphone jack socket and the portable device is configured to combine the beacon signal with an audio signal provided by an application executing on the portable device to generate a signal transmitted to the circuit using the microphone jack socket.

\* \* \* \* \*

UNITED STATES PATENT AND TRADEMARK OFFICE
CERTIFICATE OF CORRECTION

| | | |
|---|---|---|
| PATENT NO. | : 9,942,848 B2 | Page 1 of 1 |
| APPLICATION NO. | : 14/562111 | |
| DATED | : April 10, 2018 | |
| INVENTOR(S) | : Jefferson Lim Gokingco et al. | |

It is certified that error appears in the above-identified patent and that said Letters Patent is hereby corrected as shown below:

In the Claims

In Column 8, Line 16, please insert a --,-- after "level".

Signed and Sealed this
Nineteenth Day of June, 2018

Andrei Iancu
*Director of the United States Patent and Trademark Office*